(12) United States Patent
Fehn

(10) Patent No.: US 7,053,141 B2
(45) Date of Patent: May 30, 2006

(54) ORGANOSILICONE COMPOUNDS HAVING ALKYNOL GROUPS AND THE USE THEREOF IN CROSSLINKABLE MATERIALS

(75) Inventor: Armin Fehn, Mehring (DE)

(73) Assignee: Wacker-Chemie GmbH, Munich (DE)

( * ) Notice: Subject to any disclaimer, the term of this patent is extended or adjusted under 35 U.S.C. 154(b) by 0 days.

(21) Appl. No.: 10/718,322

(22) Filed: Nov. 20, 2003

(65) Prior Publication Data

US 2004/0116566 A1 Jun. 17, 2004

(30) Foreign Application Priority Data

Dec. 12, 2002 (DE) ................ 102 58 126

(51) Int. Cl.
*C08K 5/5415* (2006.01)
*C08L 83/00* (2006.01)

(52) U.S. Cl. .............. 524/265; 524/266; 524/268; 524/588; 528/15; 528/29; 528/31; 528/32

(58) Field of Classification Search ............. 528/15, 528/25–29, 31, 32; 524/588
See application file for complete search history.

(56) References Cited

U.S. PATENT DOCUMENTS

| | | | | |
|---|---|---|---|---|
| 3,989,667 A | * | 11/1976 | Lee et al. | 525/478 |
| 4,032,502 A | * | 6/1977 | Lee et al. | 523/212 |
| 4,329,275 A | | 5/1982 | Hatanaka et al. | |
| 4,382,057 A | * | 5/1983 | Tolentino | 264/328.2 |
| 4,877,820 A | * | 10/1989 | Cowan | 523/222 |
| 5,151,473 A | * | 9/1992 | Herzig | 525/474 |
| 5,607,992 A | * | 3/1997 | Chiba et al. | 524/190 |
| 5,945,475 A | | 8/1999 | Yamada et al. | |

FOREIGN PATENT DOCUMENTS

| | | |
|---|---|---|
| DE | 1 669 965 | 10/1971 |
| EP | 0 490 523 A2 | 6/1992 |

OTHER PUBLICATIONS

"Enantioselective Total Synthesis of Nicandrenones", Corey et al., J. Am. Chem. Soc. (2000) 122, 9044-45.*

"The Synthesis of Deoxyfusapyrone. 1. An Approach to the Pyrone Moiety", Organ et al., J. Org Chem (2002) 67, 7847-51.*

English Derwent Abstract AN 1968-97127P [00] corres. to DE 1 669 965.

J. Am. Chem. Soc. 1999; 121, pp. 3693-3703.

D. Miller, J. Chem. Soc. (C) (1969), pp. 12-15.

Yoshimura, F. et al., Tetrahedron Letters, vol. 40, No. 47, Nov. 19, 1999, pp. 8281-8285.

Magriotis, M. et al., Tetrahedron Letters, vol. 32, No. 43, 1991, pp. 6085-6088.

Gooding, O.W. et al., "Enantioselective Formation of Functionalized 1,3-Disubstituted Allenes: Synthesis of α-Allenic ω-Carbomethoxy Alcohols of High Optical Purity," Journal of Organic Chemistry, vol. 56, No. 3, 1991, pp. 1083-1088.

Guanti, G. et al., "Synthesis of 4-Vinyl Substituted β-Lactams of the Oxamazin Family," Tetrahedron, vol. 44, No. 12, 1988, pp. 3685-3692.

Boutin, R. et al., "α-Amino Acid Derivatives as Chiral Educts for Asymmetric Products, Synthesis of Sphingosine from α-Amino-α, β-ynones," Journal of Organic Chemistry, vol. 51, No. 26, 1986, pp. 5320-5327.

* cited by examiner

*Primary Examiner*—Marc S. Zimmer
(74) *Attorney, Agent, or Firm*—Brooks Kushman P.C.

(57) ABSTRACT

Organosilicon compounds having alkynol groups and containing units of the formula

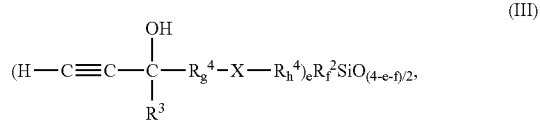

where $R^3$ and $R^2$ are optionally substituted hydrocarbon radicals, $R^4$ are divalent organic radicals, and X is a linking group are useful in addition crosslinkable compositions. The compositions exhibit long pot life and yet also exhibit excellent cure, and are useful, inter alia, in preparing molded articles and coatings.

16 Claims, No Drawings

ORGANOSILICONE COMPOUNDS HAVING ALKYNOL GROUPS AND THE USE THEREOF IN CROSSLINKABLE MATERIALS

BACKGROUND OF THE INVENTION

1. Field of the Invention

The present invention relates to organosilicon compounds having alkynol groups, processes for the preparation thereof, the use thereof in silicone materials crosslinkable by addition of Si-bonded hydrogen at an aliphatic carbon-carbon multiple bond, and moldings produced therefrom.

2. Background Art

Addition-crosslinking silicone materials crosslink through reaction of aliphatically unsaturated groups with Si-bonded hydrogen (hydrosilylation) in the presence of a catalyst, typically a platinum compound. After mixing of the individual components, a ready-to-use material is obtained which has a very limited pot life, or processing time, at room temperature, since the crosslinking reactions occur even at room temperature. This necessitates, on the one hand, use of the compositions rapidly following processing, and on the other hand, frequent cleaning of the storage containers, metering units, processing machines, etc., since residual material, for example that deposited through back-mixing or adhesion to equipment walls, finally gels.

Considerable attempts have therefore been made to suppress premature onset of the crosslinking reaction at room-temperature by means of "inhibitors." Methods of lengthening the pot life of addition-crosslinking materials include the use of inhibitors which seriously reduce the activity of the platinum catalyst at room temperature. Examples include phosphorus compounds in combination With peroxides as disclosed in U.S. Pat. No. 4,329,275 and azodicarbonyl compounds as disclosed in EP-A-490 523. The action of these types of inhibitors is based on the addition of "platinum poisons", such as nitrogen, phosphorus or sulfur compounds to the addition-crosslinking material. Although it is thus possible to considerably increase the pot life at room temperature in some cases, a disadvantageous effect on the elevated temperature crosslinking behavior is also inevitably associated with the increased pot life, i.e. the crosslinking rates at elevated temperatures also decrease considerably. The increase in crosslinking time results in higher production costs.

Another type of inhibitor comprises organic compounds or organosilicon compounds having at least one —C≡C- group as disclosed in DE-B-1 669 965. Alkynyl alcohols and alkynyloxysilanes are described therein, inter alia, as inhibitors. These inhibitors have the advantage that the crosslinking characteristics at elevated temperatures is less adversely affected as compared to the abovementioned catalyst poisons. However, even with these alkynyl inhibitors, either the pot lives as a film in air and/or in bulk, are too short, or the crosslinking rate is too slow. Moreover, since they are monomeric compounds, the inhibitors have a relatively low boiling point and hence a high vapor pressure, so that inhibitor may evaporate even during storage, thus adversely affecting the pot life. U.S. Pat. No. 5,945,475 describes the use of an alkynyl alcohol in combination with a linear siloxane which contains alkoxy groups having aliphatic triple bonds; the alkynols are reacted with siloxanes so that free hydroxyl groups are no longer present in the end product, since the alkynol bonds to the siloxane via the hydroxyl group, generating siloxanes having alkynyloxy groups. Disadvantages are that two inhibitors have to be employed, one of which is a relatively volatile monomeric alkynol having the problems described above. Furthermore, the inhibition effect of the siloxanes containing alkynyloxy groups is only very weak (cf. U.S. Pat. No. 5,945,475, comparative example 2), and as a result, the ratio of pot life or thin-film pot life at room temperature to crosslinking rate is not optimal.

SUMMARY OF THE INVENTION

It has now been surprisingly discovered that efficient inhibition of room temperature crosslinking in addition crosslinkable organosilocane compositions coupled with maintenance of crosslinking ability at elevated temperatures is facilitated by use of inhibitors comprising silanes or siloxanes containing 1-hydroxy-1-alkynyl groups linked to the silane or siloxane via a divalent organic radical.

DETAILED DESCRIPTION OF THE PREFERRED EMBODIMENT(S)

The present invention thus relates to organosilicon compounds having alkynol groups and comprising units of the formula

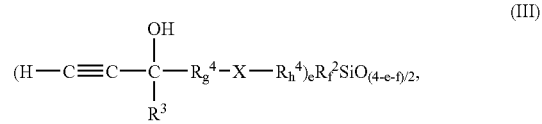

in which $R^2$ are identical or different and are a hydrogen atom, a radical —$OR^5$, or an optionally substituted hydrocarbon radical, $R^3$ are identical or different and are a hydrogen atom, a halogen atom, a radical —$OR^5$, or a monovalent, optionally substituted hydrocarbon radical, $R^4$ are identical or different and are a divalent organic radical, X may be identical or different and are —O—, —S—, —OC(=O)—, —N($R^6$)— or —N($R_6$)—C(=O)—, $R^5$ are identical or different and are a hydrogen atom or monovalent, optionally substituted hydrocarbon radical, $R^6$ are identical or different and are a hydrogen atom or a monovalent, optionally substituted hydrocarbon radical, e is 0, 1, 2 or 3, f is 0, 1, 2 or 3, g is 0 or an integer and h is 0 or an integer, with the proviso that the sum e+f is less than or equal to 4 and the organosilicon compound has at least one unit of the formula (III) where e is not zero.

The organosilicon compounds according to the invention may be both silanes, i.e. compounds of the formula (III) where e+f=4, or siloxanes, i.e. compounds containing units of the formula (III) where e+f≦3. Preferably, the organosilicon compounds according to the invention are organopolysiloxanes, in particular those which consist of essentially units of the formula (III), or consist of units of the formula (III). In the context of the present invention, the term organopolysiloxane is intended to include polymeric, oligomeric and dimeric siloxanes.

If the radicals $R^2$, $R^3$ and $R^4$ are substituted hydrocarbon radicals, preferred substituents are the halogens F, Cl, Br and I; cyano radicals; —$NR^6_2$; O; S; N; and P, and groups —$OR^6$, in which $R^6$ has the meaning stated above therefor.

Examples of $R^2$ are the examples as mentioned below for R and $R^1$. Preferably, radical $R^2$ is a hydrogen atom, —$OCH_3$, —$OCH_2CH_3$ or an optionally substituted hydrocarbon radical having 1 to 24 carbon atoms, more preferably a hydrogen atom or an optionally substituted hydrocarbon radical having 1 to 8 carbon atoms, in particular, the phenyl, the 3,3,3-trifluoropropyl, or the methyl radical.

Examples of $R^3$ are alkyl radicals such as the methyl, ethyl, n-propyl, isopropyl, 1-n-butyl, 2-n-butyl, isobutyl, tert-butyl, n-pentyl, isopentyl, neopentyl and tert-pentyl radicals, hexyl radicals such as the n-hexyl radical, heptyl radicals such as the n-heptyl radical, octyl radicals such as the n-octyl radical and isooctyl radicals such as the 2,2,4-trimethylpentyl radical, nonyl radicals such as the n-nonyl radical, decyl radicals such as the n-decyl radical, cycloalkyl radicals such as the cyclopropyl, cyclopentyl, cyclohexyl, cycloheptyl, and methylcyclohexyl radicals, unsaturated radicals such as the ethynyl, vinyl, allyl, 5-hexenyl, 7-octenyl, cyclohexenyl and styryl radicals, aryl radicals such as phenyl radicals, o-, m- or p-tolyl radicals, xylyl radicals and ethylphenyl radicals, and aralkyl radicals such as the benzyl radical and the α- and β-phenylethyl radicals.

Further examples of $R^3$ are hydroxyl, methoxy, ethoxy, isopropoxy, butoxy and phenoxy radicals, while examples of halogenated radicals $R^3$ are haloalkyl radicals such as the 3,3,3-trifluoro-n-propyl radical, the 2,2,2,2',2',2',hexafluoroisopropyl radical, and the heptafluoroisopropyl radical, and haloaryl radicals such as the o-, m-, and p-chlorophenyl radicals.

Radical $R^3$ is preferably a hydrogen atom, a radical —$OR^1$ where $R^5$ has the abovementioned meaning or a hydrocarbon radical having 1 to 24 carbon atoms, more preferably a hydrogen atom, hydroxyl radical, methoxy radical or hydrocarbon radical having 1 to 8 carbon atoms, in particular, a hydrogen atom, the methyl radical, the phenyl radical, or the ethyl radical.

Examples of $R^4$ are divalent radicals such as —$CH_2$—, —$CH(CH_3)$—, —$C(CH_3)_2$—, —$CH(CH_3)$—$CH_2$—, —$C_6H_4$—, —$CH(Ph)$-$CH_2$—, —$C(CF_3)_2$—, —$(CH_2)_n$— $C_6H_4$—$(CH_2)_n$—, —$(CH_2)_n$—$C_6H_4$—$C_6H_4$—$(CH_2)_n$—, —$(CH_2O)_m$—, —$OC(=O)$—$(CH_2)_n$—, —$(CH_2)_n$—, —$(CH_2CH_2O)_m$— and —$(CH_2)_n$—$O_x$—$C_6H_4$—$SO_2$—$C_6H_4$—$O_x$—O—$(CH_2)_n$—, in which x is 0 or 1, n and m are identical or different integers from 0 to 10, and Ph is a phenyl radical. Radical $R^4$ is preferably a divalent organic radical having 1 to 24 carbon atoms, more preferably —$CH_2$—, —$(CH_2)_3$—, —$C_6H_4$—, or —$CH(CH_3)$—, and in particular —$CH_2$—, $C_6H_4$ and —$(CH_2)_3$—.

Examples of radical $R^5$ are the examples stated for $R^3$ or a hydrogen atom, hydrocarbon radicals having 1 to 24 carbon atoms being preferred, and a hydrogen atom and the methyl, 2-ethylhexyl and phenyl radicals being most preferred.

Examples of radical $R^6$ are the examples stated for $R^3$. $R^6$ is preferably a hydrogen atom or a hydrocarbon radical having 1 to 20 carbon atoms, more preferably a hydrogen atom or a hydrocarbon radical having 1 to 8 carbon atoms, and in particular, a hydrogen atom, or a methyl or ethyl radical.

Radical X is preferably —O—, —$OC(=O)$— or —$N(R^6)$—$C(=O)$— where $R^6$ has the abovementioned meaning, —O— being particularly preferred.

In the silanes and siloxanes of formula (III), e is preferably 0 or 1; f is preferably 1, 2 or 3; g is preferably 0 or an integer from 1 to 10, more preferably from 1 to 5; and h is 0 or an integer from 1 to 10, more preferably 0, 1 or 3.

If the organosilicon compounds of formula (III) are organopolysiloxanes, these preferably have a viscosity of from 1.0 to 30,000,000 $mm^2/s$, more preferably from 5.0 to 60,000 $mm^2/s$, in each case at 25° C. The organosilicon compounds are preferably those which are nonvolatile and have very low vapor pressures, and preferably those which are homogeneously soluble in liquid polydimethylsiloxanes.

Examples of the organosilicon compounds according to the invention are (H—C≡C—$C(R^3)(OH)$—$R^4_g$—X—$R^4_h$) $R^2_3Si$, (H—C≡C—$C(R^3)(OH)$—$R^4_g$—X—$R^4_h$)$_2R^2_2Si$, (H—C≡C—$C(R^3)(OH)$—$R^4_g$—X—$R^4_h$)$_3R^2Si$ (H—C≡C—$C(R^3)(OH)$—$R^4_g$—O)$R^2_3Si$, (H—C≡C—$C(R^3)(OH)$—$R^4_g$—O)$_2R^2_2Si$, and (H—C≡C—$C(R^3)(OH)$—$R^4_g$—O)$_3R^2Si$, in which $R^2$, $R^3$, $R^4$, X, g and h have the abovementioned meanings. Further examples are organosilanes having molecular weights of from about 130 to 2000 g/mol and in which X is O or —$OC(=O)$—, such as H—C≡C—C(OH)($CH_3$)—$C_6H_4$—O—$CH_2$—$SiMe_3$, H—C≡C—C(OH)($CH_3$)—$C_6H_4$—O—$CH_2$—$SiMe_2$—$(CH_2)_7$—$CH_3$, H—C≡C—C(OH)($CH_3$)—$C_6H_4$—O—$SiMe_3$, H—C≡C—C(OH)($CH_3$)—$C_6H_4$—O—$SiMe_2$—$(CH_2)_{17}$—$CH_3$, H—C≡C—C(OH)($CH_3$)—$CH_2$—O—$SiMe_3$, H—C≡C—C(OH)($CH_2CH_3$)—$CH_2$—O—$SiMe_2$—$(CH_2)_{17}$—$CH_3$, H—C≡C—C(OH)($CH_3$)—$CH_2$—O—$SiMe_2OMe$, H—C≡C—C(OH)(Ph)-$(CH_2)_3$—O—$(CH_2)_3$—$SiMe_2OMe$, H—C≡C—C(OH)(H)—$(CH_2)_3$—O—$C(=O)(CH_2)_2$—$SiMe_3$ and H—C≡C—C(OH)(H)—$(CH_2)_3$—O—$C(=O)$—$C(=O)$—O—$(CH_2)_3$—$SiMe_3$ where Me is the methyl radical and Ph is the phenyl radical.

Further examples of the organosilicon compounds according to the invention are low molecular weight organosiloxanes, such as (H—C≡C—$C(R^3)(OH)$—$R^4_g$—X—$R^4_h$)—$SiMe_2$—O—$SiMe_3$, cyclic polydimethylsiloxanes which contain (H—C≡C—$C(R^3)(OH)$—$R^4_g$—X—$R^4_h$)—$SiR^2$— or (H—C≡C—$C(R^3)(OH)$—$R^4_g$—X—$R^4_h$)$_2$—Si groups or relatively high molecular weight to high molecular weight linear, branched or resin-like polydimethylsiloxanes having terminal (H—C≡C—C(R3)(OH)—$R^4_g$—X—$R^4_h$)$R^2_2SiO_{1/2}$ groups and/or (H—C≡C—$C(R^3)(OH)$—$R^4_g$—X—$R^4_h$) radicals in the chain, and molecular weights of, for example, $5·10^2$ g/mol, $10^3$ g/mol, or $10^5$ g/mol (number average, determined by means of NMR), $R^2$, $R^3$, $R^4$, X, g and h having the above-mentioned meanings.

The organosilicon compounds according to the invention are preferably low molecular weight alkynol functional oligosiloxanes, cyclic polydimethylsiloxanes which contain (H—C≡C—$C(R^3)(OH)$—$R^4_g$—$X^1$—$R^4_h$)—$SiR^2$— or (H—C≡C—$C(R^3)(OH)$—$R^4_g$—$X^1$—$R^4_h$)$_2$—Si groups or relatively high molecular weight linear, branched or resin-like polydimethylsiloxanes having terminal (H—C≡C—C(R3)(OH)—$R^4_g$—$X^1$—$R^4_h$)$R^2_2SiO_{1/2}$ groups and/or (H—C≡C—$C(R^3)(OH)$—$R^4_g$—$X^1$—$R^4_h$) radicals in the chain and molecular weights of, for example, from $5·10^2$ g/mol to $6·10^4$ g/mol (number average, determined by means of NMR) and in which $X^1$ is —O— or —$OC(=O)$—, more preferably cyclic polydimethylsiloxanes which contain (H—C≡C—C(R3)(OH)—$R^4_g$—$X^1$—$R^4_h$)—$SiR_2$ groups, or low molecular weight or relatively high molecular weight, linear, branched or resin-like polydimethylsiloxanes having terminal (H—C≡C—$C(R3)(OH)$—$R^4_g$—$X^1$—$R^4_h$) $R^2_2SiO_{1/2}$ groups and/or (H—C≡C—$C(R^3)(OH)$—$R^4_g$—$X^1$—$R^4_h$) radicals in the chain, and molecular weights of, for example, from $5·10^2$ g/mol to $2·10^4$ g/mol (number average, determined by means of NMR) and in which $X^1$ is —O—, $R^2$, $R^3$, $R^4$, X, g and h having the above-mentioned meanings.

The organosilicon compounds which have alkynol groups can be prepared by any desired method. For example, the organosilicon compounds in which X is —O—, —S—, —OC(=O)—, —N($R^6$)— or —N($R^6$)—C(=O)— and h is 0 are preferably prepared by reacting organosilicon compounds having Si—Cl bonds, such as chlorosilanes or chlorosiloxanes, with alkynols of the general formula

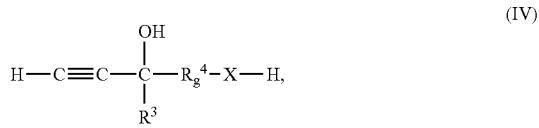

in which $R^3$, $R^4$, X and g have the abovementioned meanings, in the presence of bases such as triethylamine, pyridine or potassium carbonate (process 1). Advantageously, in this reaction, the base is first added to the alkynol of the formula (IV), optionally dissolved in a solvent, at temperatures between −50 and +50° C. and then the organosilicon compounds having Si—Cl bonds, optionally also dissolved in a solvent, are added. After the end of the reaction, the product is advantageously separated from the base hydrochloride and any solvent. The product can, if desired, be purified by methods known per se, such as by distillation, recrystallization or washing with solvents.

Furthermore, the organosilicon compounds in which X is O and h is zero preferably can also be prepared by reacting alkynols of the formula (IV) in which X is O, i.e. H—C≡C—C(OH)($R^3$)—$R^4_g$—O—H, with organosilicon compounds which contain OH or organyloxy groups, optionally in the presence of acidic or basic or metal-containing catalysts (process 2). The organosilicon compounds can also be obtained by reacting nonfunctionalized organosiloxanes with H—C≡C—C(OH)($R^3$)—$R^4_g$—O—H in the presence of acidic, basic or metal-containing catalysts.

The organosilicon compounds in which X is —O—, —S—, —OC(=O)—, —N($R^6$)— or —N($R^6$)—C(=O)— and h is not 0 are preferably prepared by reacting alkynols of the general formula (IV) with organosilicon compounds containing units of the formula

in which Y are identical or different and are F, Cl, Br, I, —$OSO_2$—$C_6H_4$—$CH_3$, —$OSO_2$—$C_6H_4$—Br or —$OSO_2$—$CF_3$, and $R^2$, $R^4$, e, f and h have the meanings stated above, in the presence of bases such as, triethylamine, pyridine, potassium carbonate, sodium hydride or BuLi (process 3). Advantageously, the base is first added to the alkynol of the formula (IV), optionally dissolved in a solvent, at temperatures between −100 and +50° C., and then the organosilicon compounds containing units of the formula (V), optionally also dissolved in a solvent, are added at temperatures between −100 and +150° C.

Alternatively, the organosilicon compounds can be prepared by reacting alkynols of the formula

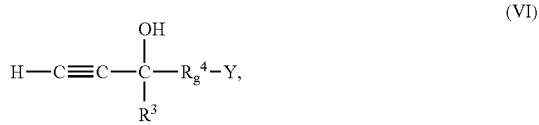

in which Y, $R^3$, $R^4$ and g have the meanings stated above, with organosilicon compounds containing units of the formula

in which X, $R^2$, $R^4$, e, f and h have one of the meanings stated above (process 4).

The organosilicon compounds in which X is —O—C(O)— can furthermore advantageously be obtained by reacting an acid chloride or diacid chloride with an alcohol in the presence of a base.

In all the processes which are described above, the products obtained after the end of the reaction can, if desired, be purified by methods known per se, such as by distillation, recrystallization or washing with solvents. Furthermore, in all the above processes, the organosilicon compounds obtained can subsequently be further reacted by reactions known per se which are typical for silane and siloxane chemistry, such as equilibration, ligand exchange, transesterification, disproportionation, coproportionation, and condensation.

The organosilicon compounds of the invention, or which are prepared by the processes of the invention can be used for all purposes for which organosilicon compounds having alkynol groups have also been used to date. In particular, they are suitable for use in all processes for the reaction of compounds having Si-bonded hydrogen with organic or organosilicon compounds having carbon-carbon multiple bonds in the presence of hydrosilylation catalysts.

The present invention furthermore relates to crosslinkable materials comprising:

(A) compounds which have radicals having aliphatic carbon-carbon multiple bonds, (B) organosilicon compounds having Si-bonded hydrogen atoms, (C) organosilicon compounds having alkynol groups and containing units of the formula (III) and (D) a catalyst which promotes the addition of Si-bonded hydrogen at an aliphatic multiple bond.

It is known that the compounds (A) and (B) used in the crosslinkable materials according to the invention are chosen so that crosslinking is possible. Thus, generally, for example, but not by limitation, compound (A) may have at least two aliphatically unsaturated radicals and siloxane (B) may have at least three Si-bonded hydrogen atoms, or compound (A) may have at least three aliphatically unsaturated radicals and siloxane (B) may have at least two Si-bonded hydrogen atoms.

The compound (A) preferably comprises silicon-free organic compounds having at least two aliphatically unsaturated groups as well as organosilicon compounds having at least two aliphatically unsaturated groups. Examples of organic compounds which can be used as component (A) in the crosslinkable materials of the invention include 1,3,5-trivinylcyclohexane, 2,3-dimethyl-1,3-butadiene, 7-methyl-3-methylene-1,6-octadiene, 2-methyl-1,3-butadiene, 1,5-hexadiene, 1,7-octadiene, 4,7-methylene-4,7,8,9-tetrahydroindene, methylcyclopentadiene, 5-vinyl-2-norbornene, bicyclo[2.2.1]hepta-2,5-diene, 1,3-diisopropenylbenzene, polybutadiene containing vinyl groups, 1,4-divinylcyclohexane, 1,3,5-triallylbenzene, 1,3,5-trivinylbenzene, 1,2,4-trivinylcyclohexane, 1,3,5-triisopropenylbenzene, 1,4-divinylbenzene, 3-methyl-1,5-heptadiene, 3-phenyl-1,5-hexadiene, 3-vinyl-1,5-hexadiene and 4,5-dimethyl-4,5-diethyl-1,7-octadiene, N,N'-methylenebisacrylamide, 1,1,1-tris(hydroxymethyl)propane triacrylate, 1,1,1-tris(hydroxymethyl)propane trimethacrylate, tripropylene glycol diacrylate, diallyl ether, diallylamine, diallyl carbonate, N,N'-diallylurea, triallylamine, tris(2-methylallyl)amine, 2,4,6-triallyloxy-1,3,5-triazine, triallyl-s-triazine-2,4,6-(1H,3H,5H)-trione, diallylmalonic esters, polyethylene glycol diacrylate, polyethylene glycol dimethacrylate and poly(propylene glycol)methacrylate.

Component (A) preferably comprises aliphatically unsaturated organosilicon compounds, it being possible to use all aliphatically unsaturated organosilicon compounds used to date in addition-crosslinking materials or those hereafter developed, including, for example, silicone block copolymers having urea segments, silicone block copolymers having amide segments, imide segments, and/or ester-amide segments, polystyrene segments, silarylene segments, carborane segments, as well as silicone graft copolymers having ether groups, and combinations of these as well.

Organosilicon compounds (A) preferably contain SiC-bonded radicals with aliphatic carbon-carbon multiple bonds, and are linear or branched organopolysiloxanes comprising units of the formula

in which
R are identical or different and are radicals free of aliphatic carbon-carbon multiple bonds,
$R^1$ are identical or different and are monovalent, optionally substituted, SiC-bonded hydrocarbon radicals having an aliphatic carbon-carbon multiple bond,
a is 0, 1, 2 or 3 and
b is 0, 1 or 2, with the proviso that the sum a+b is less than or equal to 3 and on average at least 2 radicals $R^1$ are present per molecule.

Radical R may comprise monovalent or polyvalent radicals, the polyvalent radicals, such as bivalent, trivalent and tetravalent radicals, then linking a plurality of silyloxy units of the formula (I), such as, for example, two, three or four said units, to one another.

R may also comprise monovalent radicals —F, —Cl, —Br, —$OR^6$ and SiC-bonded, optionally substituted hydrocarbon radicals which may be interrupted by oxygen atoms or the group —C(O)—, and divalent radicals Si-bonded at both ends according to formula (I).

If a radical R comprises an SiC-bonded, substituted hydrocarbon radical, preferred substituents are halogen atoms, phosphorus-containing radicals, cyano radicals, —$OR^6$, —$NR^6$—, —$NR^6_2$ and —$C_6F_5$ in which $R^6$ has the above-mentioned meaning.

Examples of radicals R are alkyl radicals such as the methyl, ethyl, n-propyl, isopropyl, n-butyl, isobutyl, tert-butyl, n-pentyl, isopentyl, neopentyl and tert-pentyl radicals, hexyl radicals such as the n-hexyl radical, heptyl radicals such as the n-heptyl radical, octyl radicals such as the n-octyl radical and isooctyl radicals such as the 2,2,4-trimethylpentyl radical, nonyl radicals such as the n-nonyl radical, decyl radicals such as the n-decyl radical, dodecyl radicals such as the n-dodecyl radical, and octadecyl radicals such as the n-octadecyl radical, cycloalkyl radicals such as cyclopentyl, cyclohexyl, cycloheptyl and methylcyclohexyl radicals, aryl radicals such as the phenyl, naphthyl, anthryl and phenanthryl radical, alkaryl radicals such as the o-, m-, and p-tolyl radicals, xylyl radicals and ethylphenyl radicals, and aralkyl radicals such as the benzyl radical and the α- and the β-phenylethyl radicals.

Examples of substituted radicals R are haloalkyl radicals, such as the 3,3,3-trifluoro-n-propyl radical, the 2,2,2',2',2'-hexafluoroisopropyl radical and the heptafluoroisopropyl radical, and haloaryl radicals such as the o-, m- and p-chlorophenyl radicals.

Examples of divalent radicals R which are Si-bonded at both ends according to formula (I) are those which are derived from the monovalent examples stated above for radical R in such a way that an additional bond is produced by substitution of a hydrogen atom. Examples of such radicals are —$(CH_2)_o$—, —$CH(CH_3)$—, —$C(CH_3)_2$—, —$CH(CH_3)$—$CH_2$—, —$C_6H_4$—, —$CH(Ph)$-$CH_2$—, —$C(CF_3)_2$—, —$(CH_2)_o$—$C_6H_4$—$(CH2)_o$—, —$(CH_2)_o$—$C_6H_4$—$C_6H_4$—$(CH_2)_o$—, —$(CH_2O)_p$—, —$(CH_2CH_2O)_p$—, —$(CH_2)_o$—$O_y$—$C_6H_4$—$SO_2$—$C_6H_4$—$O_y$—$(CH_2)_o$—, y being 0 or 1, o and p being identical or different integers from 0 to 10, and Ph being a phenyl radical.

Radical R is preferably a monovalent SiC-bonded, optionally substituted hydrocarbon radical free of aliphatic carbon-carbon multiple bonds and having 1 to 18 carbon atoms, more preferably a monovalent SiC-bonded hydrocarbon radical free of aliphatic carbon-carbon multiple bonds and having 1 to 6 carbon atoms, and in particular, the methyl or phenyl radical.

Radical $R^1$ may be any desired group capable of undergoing an addition reaction (hydrosilylation) with an Si H-functional compound. If radical $R^1$ comprises an SiC-bonded, substituted hydrocarbon radical, preferred substituents are halogen atoms, cyano radicals and —$OR^6$, $R^6$ having one of the above-mentioned meanings. Radical $R^1$ preferably comprises alkenyl and alkynyl groups having 2 to 16 carbon atoms, such as the vinyl, allyl, methallyl, 1-propenyl, 5-hexenyl, ethynyl, butadienyl, hexadienyl, cyclopentenyl, cyclopentadienyl, cyclohexenyl, vinylcyclohexylethyl, divinylcyclohexylethyl, norbornenyl, vinylphenyl and styryl radicals, with vinyl, allyl and hexenyl radicals being particularly preferred.

The molecular weight of the component (A) may vary within wide limits, for example between $10^2$ and $10^6$ g/mol. Thus, the component (A) may be, for example, a relatively low molecular weight alkenyl-functional oligosiloxane, such as 1,2-divinyltetramethyldisiloxane, but may also be a highly polymeric polydimethylsiloxane having Si-bonded vinyl groups in the chain or terminal Si-bonded vinyl groups, for example having a molecular weight of $10^5$ g/mol (number average, determined by means of NMR). The structure of the molecules forming the component (A) may vary; in particular the structure of a relatively high molecular weight, i.e. oligomeric or polymeric siloxane, may be linear, cyclic, branched, resin-like, or network-like. Linear and cyclic polysiloxanes are preferably composed of units of the formula $R_3SiO_{1/2}$, $R^1R_2SiO_{1/2}$, $R^1SiO_{2/2}$ and $R_2SiO_{2/2}$, R and $R^1$ having the abovementioned meanings. Branched and network-like polysiloxanes additionally contain trifunctional and/or tetrafunctional units, those of the formulae $RSiO_{3/2}$, $R^1SiO_{3/2}$ and $SiO_{4/2}$ being preferred. Of course, mixtures of different siloxanes fulfilling the criteria of component (A) may also be used.

The use of vinyl-functional, substantially linear polydiorganosiloxanes having a viscosity of from 0.6 to 500,000,000 $mm^2$/s, more preferably from 10 to 50,000,000 $mm^2$/s, in each case at 25° C., is particularly preferred as component (A).

All hydrogen-functional organosilicon compounds which have also been used to date in addition-crosslinkable materials or those hereafter developed can be employed as organosilicon compound (B). Of course, mixtures of different siloxanes fulfilling the criteria of component (B) may also be used. In particular, the molecules forming the component (B) may optionally also contain aliphatically unsaturated groups in addition to the obligatory SiH groups.

Linear, cyclic or branched organopolysiloxanes containing units of the formula $$R^7_c H_d SiO_{(4-c-d)/2} \quad (II)$$

in which
$R^7$ are identical or different and have the meaning stated above for radical R,
c is 0, 1, 2 or 3 and
d is 0, 1 or 2,
with the proviso that the sum c+d is less than or equal to 3 and on average at least two Si-bonded hydrogen atoms are present per molecule, are preferably used as organosilicon compounds (B) which have Si-bonded hydrogen atoms.

The organopolysiloxane (B) preferably contains Si-bonded hydrogen in the range of from 0.01 to 1.7 percent by weight, based on the total weight of the organopolysiloxane (B). The molecular weight of the component (B) can likewise vary within wide limits, for example between $10^2$ and $10^6$ g/mol. Thus, the component (B) may be, for example, a relatively low molecular weight SiH-functional oligosiloxane, such as tetramethyldisiloxane, but may also a highly polymeric polydimethylsiloxane having SiH groups in the chain and/or terminal SiH, groups or a silicone resin having SiH groups. The structure of the molecules forming the component (B) may also vary; in particular, the structure of a relatively high molecular weight, i.e. oligomeric or polymeric, SiH-containing siloxane may be linear, cyclic, branched, resin-like, or network-like. Linear and cyclic polysiloxanes are preferably composed of units of the formulae $R^7_3 SiO_{1/2}$—, $HR^7_2 SiO_{1/2}$, $HR^7 SiO_{2/2}$ and $R^7_2 SiO_{2/2}$, $R^7$ having the abovementioned meaning. Branched and network-like polysiloxanes additionally contain trifunctional and/or tetrafunctional units, those of the formulae $R^7 SiO_{3/2}$, $HSiO_{3/2}$ and $SiO_{4/2}$ being preferred.

The component (B) most preferably comprises low molecular weight, SiH-functional compounds, such as 1,1,3,3-tetramethyldisiloxane, tetrakis(dimethylsiloxy)silane, 1,1,1,3,5,5,5-heptamethyltrisiloxane and tetramethylcyclotetrasiloxane, and relatively high molecular weight, SiH-containing siloxanes, such as poly(hydrogenmethyl)siloxane and poly(dimethylhydrogenmethyl)siloxane having a viscosity at 25° C. of from 1 to 1,000,000 mm²/s, or analogous SiH-containing compounds in which some of the methyl groups have been replaced by 3,3,3-trifluorpropyl or phenyl groups.

The components (A) and (B) are commercial products or can be prepared by processes customary in chemistry.

Component (B) is preferably contained in the crosslinkable materials according to the invention in an amount such that the molar ratio of SiH groups to aliphatically unsaturated groups is from 0.1 to 20, more preferably from 0.8 to 5.0. The crosslinkable materials of the invention preferably contain component (C) in amounts of from 0.0001 to 70% by weight, more preferably from 0.02 to 10% by weight, based in each case on component (A).

All catalysts which have also been used to date in materials crosslinkable by addition of Si-bonded hydrogen at an aliphatic multiple bond, or which are later developed, can be used as component (D) employed according to the invention. Component (D) preferably comprises hydrosilylation catalysts from groups 8, 9 or 10 of the Periodic Table of the Elements. Here, metals and compounds thereof, such as those of platinum, rhodium, palladium, iron, ruthenium and iridium, preferably platinum, can be used. The metals can optionally be fixed on finely divided support materials, such as active carbon, or metal oxides such as alumina or silica.

Preferable hydrosilylation catalysts (D) are platinum and platinum compounds, more preferably those platinum compounds which are soluble in polyorganosiloxanes. For example, the platinum-olefin complexes of the formulae $(PtCl_2 \cdot olefin)_2$ and $H(PtCl_3 \cdot olefin)$ can be used as soluble platinum compounds, alkenes having 2 to 8 carbon atoms, such as ethylene, propylene, isomers of butylene and of octene or cycloalkanes having 5 to 7 carbon atoms, such as cyclopentene, cyclohexene and cycloheptene, preferably being employed. Further soluble platinum catalysts are the platinum-cyclopropane complexes of the formula $(PtCl_2 C_3 H_6)_2$, the reaction product of hexachloroplatinic acid with alcohols, ethers and aldehydes or mixtures thereof, or the reaction product of hexachloroplatinic acid with methylvinylcyclotetrasiloxane in the presence of sodium bicarbonate in ethanolic solution. Platinum catalysts having phosphorus, sulfur and amine ligands may also be used, such as, for example, $(Ph_3P)_2 PtCl_2$. Complexes of platinum with vinylsiloxanes, such as sym-divinyltetramethyldisiloxane, are particularly preferred as component (D).

The amount of the hydrosilylation catalyst (D) depends on the desired crosslinking rate, on the respective use, and on costs of factors. The crosslinkable materials of the invention preferably contain platinum catalysts (D) in amounts such that a platinum content of from 0.05 to 500 ppm by weight (parts by weight per million parts by weight), more preferably from 0.5 to 120 ppm by weight, and in particular from 1 to 50 ppm by weight, based in each case on the total weight of the crosslinkable material results.

In addition to the components (A) to (D), the curable compositions may also contain all further substances which are useful for the preparation of addition-crosslinkable materials.

Examples of reinforcing fillers which can be used as a component (E) in the crosslinkable materials include pyrogenic or precipitated silicas having BET surface areas of at least 50 m²/g and carbon blacks and active carbons such as furnace black and acetylene black, with pyrogenic and precipitated silicas having BET surface areas of at least 50 m²/g being preferred. The silica fillers may have a hydrophilic character or may have been rendered hydrophobic by known processes. When hydrophilic fillers are employed, the addition of a water repellent is required. The content of actively reinforcing filler (E) in the crosslinkable material is preferably in the range from 0 to 70% by weight, more preferably from 0 to 50% by weight.

The crosslinkable material may optionally contain, as a component (F), further additives in an amount of from 0 to 96% by weight, preferably from 0.0001 to 40% by weight. These additives may be, for example, inactive fillers, resin-like polyorganosiloxanes which differ from the organosilicon compounds (A) and (B) and preferably consist of $R_3 SiO_{1/2}$, $SiO_{4/4}$ and/or $RSiO_{3/2}$ and optionally $R^1 R_2 SiO_{1/2}$, R and $R^1$ having the abovementioned meanings, dispersants, solvents, adhesion promoters, pigments, dyes, plasticizers, organic polymers, heat stabilizers, fillers for thermal conductivity, etc. These include additives such as quartz powder, diatomaceous earth, clays, chalk, lithopone, carbon blacks, graphite, metal oxides such as alumina and silica, metal carbonates, nitrides such as metal nitrides and boron nitride, carbides such as boron carbide and silicon carbide, metal sulfates, metal salts of carboxylic acids, metal dusts, fibers such as glass fibers and plastics fibers, plastics powders, dyes, and pigments.

Additives (G) which serve for further establishment of specific processing time, initiation temperature and crosslinking rate of the materials according to the invention may furthermore be present. These inhibitors and stabilizers are very well known in the area of addition-crosslinking materials. Examples of customary inhibitors are acetylenic alcohols, such as 1-ethynyl-1-cyclohexanol, 2-methyl-3-butyn-2-ol and 3,5-dimethyl-1-hexyn-3-ol, 3-methyl-1-dodecyn-3-ol, polymethylvinylcyclosiloxanes, such as 1,3,5,7-tetravinyltetramethyltetracyclosiloxane, low molecular weight silicone oils having methylvinyl-$SiO_{2/2}$ groups and/ or $R_2$-vinyl-$SiO_{1/2}$ terminal groups such as divinyltetramethyldisiloxane, tetravinyldimethyldisiloxane, trialkyl cyanurates, alkyl maleates such as diallyl maleates, dimethyl maleate and diethyl maleate, alkyl fumarates such as diallyl fumarate and diethyl fumarate, organic hydroperoxides such as cumyl hydroperoxide, tert-butyl hydroperoxide and pinane hydroperoxide, organic peroxides, organic sulfoxides, organic amines, diamines and amides, phosphines and phosphites, nitriles, triazoles, diaziridines, and oximes.

The crosslinkable materials are preferably those which contain
(A) compounds which have radicals having aliphatic carbon-carbon multiple bonds,
(B) organopolysiloxanes having Si-bonded hydrogen atoms,
(C) organopolysiloxanes having alkynol groups and containing units of the formula (III),
(D) at least one catalyst which promotes the addition of Si-bonded hydrogen at an aliphatic multiple bond,
(E) optionally, reinforcing fillers,
(F) optionally, further components.

If the crosslinkable materials are to be used for coatings, they are preferably those which contain
(A) compounds which have radicals having aliphatic carbon-carbon multiple bonds,
(B) organopolysiloxanes having Si-bonded hydrogen atoms,
(C) organopolysiloxanes having alkynol groups and containing units of the formula (III),
(D) at least one catalyst which promotes the addition of Si-bonded hydrogen at an aliphatic multiple bond, and
(E) pyrogenic or precipitated silicas having BET surface areas of at least 50 $m^2/g$, and/or
(F) resin-like polydimethylsiloxanes which are composed of $R_3SiO_{1/2}$, $SiO_{4/4}$ and optionally $R^1R_2SiO_{1/2}$.

The crosslinkable materials are most preferably those which consist of
(A) substantially linear compounds which have on average at least two radicals having aliphatic carbon-carbon multiple bonds,
(B) organopolysiloxanes having on average at least two Si-bonded hydrogen atoms,
(C) organopolysiloxanes having alkynol groups and containing units of the formula (III),
(D) at least one catalyst which promotes the addition of Si-bonded hydrogen at an aliphatic multiple bond,
(E) optionally, reinforcing fillers,
(F) optionally, further components, and
(G) optionally, inhibitors and/or stabilizers.

The crosslinkable materials, if desired, be dissolved, dispersed, suspended or emulsified in liquids. The crosslinkable materials can, in particular depending on the viscosity of the components and filler content, have a low viscosity and can be pourable, can have a pasty consistency, can be pulverulent or pliable, or can be highly viscous materials, as is known possible in the case of the materials frequently designated as RTV-1, RTV-2, LSR and HTV compositions among those skilled in the art. In particular, if they are highly viscous or solid, the crosslinkable materials may be prepared in the form of granules. Here the individual granular particle may contain all necessary components, or the components (D) and (B) used according to the invention may be incorporated separately into different granular particles.

The preparation of the crosslinkable materials can be effected by known processes, for example, by uniform mixing of the individual components. The method of mixing is dependent on the viscosity of (A), e.g. by use of a stirrer, a dissolver, on a roll, or in a kneader.

The components (A) to (G) may each be an individual type of such a component or a mixture of at least two different types of such a component.

The crosslinkable materials which are crosslinkable by addition of Si-bonded hydrogen at aliphatic multiple bonds can be crosslinked under the same conditions conventional materials crosslinkable by hydrosilylation reactions. Temperatures of from 50 to 220° C., more preferably from 100 to 190° C., and a pressure of the ambient atmosphere, i.e. from about 900 to 1,100 hPa, are preferred. However, higher or lower temperatures and pressures may also be used. The crosslinking can also be carried out photochemically using high-energy radiation, for example, visible light having short wavelengths or by UV light, or by using any combination of thermal and photochemical excitation.

The present invention furthermore relates to moldings produced by crosslinking the materials according to the invention. The elastomeric properties of the moldings produced according to the invention likewise cover the entire spectrum, beginning with extremely soft silicone gels through rubber-like materials to highly crosslinked silicones having glassy behavior.

The crosslinkable materials and the crosslinked products produced therefrom can be used for all purposes for which elastomers or organopolysiloxane materials crosslinkable to give elastomers may be used. This includes, for example, silicone coating and impregnation of any desired substrate, the production of shaped articles, for example by injection molding, vacuum extrusion, extrusion, casting and compression molding, for impressions, and for use as sealing compounds, embedding compounds, and potting compounds.

The organosilicon compounds having alkynol groups have the advantage that they are soluble in liquid organopolysiloxanes. Furthermore, the organosilicon compounds having alkynol groups have the advantage that alkyne oligomerizations and alkyne metathesis reactions can be carried out using suitable catalysts.

The organopolysiloxanes having alkynol groups have the further advantage that they can be thermally crosslinked to give elastomers, and can be crosslinked using alkyne oligomerization catalysts to give elastomers. Moreover, the organopolysiloxanes having alkynol groups have the additional advantage that they can be crosslinked by alkyne-alcohol addition reactions to give elastomers.

The organosilicon compounds having alkynol groups also have the advantage that their use results in silicone materials which have long pot lives in bulk and/or in thin films at room temperature in combination with fast crosslinking rates at elevated temperatures, and that their pot life and crosslinking characteristics are independent of storage.

The organopolysiloxanes having alkynol groups when used in crosslinkable materials have the advantage that they are sparingly volatile, have a low vapor pressure, and have long pot lives at room temperature, both in thin films and in bulk, and yet crosslink rapidly at elevated temperatures. Moreover, the crosslinkable materials have a long shelf life. The crosslinking characteristics do not change during storage at room temperature and ambient pressure. In the case of two-component formulations, after mixing of the two components, a crosslinkable material results whose processibility is retained over a long period at 25° C. and ambient pressure, and yet which rapidly crosslinks only at elevated temperature.

In the examples described below, all parts and percentages are based on weight, and the examples are carried out at a pressure of ambient atmosphere, i.e. at about 1,000 hPa, and at room temperature, i.e. at about 20° C., or at a temperature which results on combining the reactants at room temperature without additional heating or cooling, unless stated otherwise. All viscosity data are based on a temperature of 25° C. In the examples, Vi is vinyl radical, Me is the methyl radical, Ph is the phenyl radical, d is days, and s is seconds.

EXAMPLE 1

Preparation of a Siloxane Having Alkynol Groups (Inhibitor 1)

75 ml of toluene were added to 10 parts of 3-methyl-1-butyne-3,4-diol, prepared according to D. Miller, J. CHEM. SOC. (C) (1969) 12–15, and 10.4 parts of triethylamine. At a temperature of 0° C., 138 parts of chlorosiloxane, dissolved in 75 ml of toluene, were added dropwise over the course of 40 minutes. According to $^1$H- and $^{29}$Si-NMR, the chlorosiloxane is a siloxane polymer consisting of —O—Si(Me)$_2$—, —O—SiCl(Me)$_2$ and —O—Si(Me)$_3$ units in the molar ratio 17.7:1.01:0.99. The reaction mixture was then stirred for 4 hours at room temperature before it was filtered in order to separate off precipitated triethylammonium chloride. Finally, the toluene was removed in vacuo at room temperature. According to $^1$H-NMR and $^{29}$Si-NMR spectra, the reaction product is a siloxane polymer containing alkynol groups and consisting of —O—Si(Me)$_2$—, —O—Si(—O—CH$_2$—C(OH)(CH$_3$)—C≡C—H)(Me)$_2$ and —O—Si(Me)$_3$ units in the molar ratio 27.1:0.85:1.15.

EXAMPLE 2

50.0 parts of a vinyldimethylsilyloxy-terminated polydimethylsiloxane having a viscosity of 20 Pa·s, 0.637 part of inhibitor 1 (which corresponds to 92 mol of alkynol per mole of platinum) and 1.0 part of SiH crosslinking agent were homogeneously mixed at room temperature with the aid of a stirrer from Janke & Kunkel IKA-Labortechnik, TYPE RE 162, the SiH crosslinking agent being a copolymer comprising dimethylsilyloxy and methylhydrogensilyloxy and trimethylsilyloxy units, having a viscosity of 330 mPa·s and a content of Si-bonded hydrogen of 0.46% by weight. 0.051 part of Karstedt catalyst (based on the platinum content: about 1% strength solution in toluene) was then added with stirring. The Karstedt catalyst is a platinum-1,3-divinyl-1,1,3,3-tetramethyldisiloxane complex which is described, for example, in J. AM. CHEM. SOC., 1999, 121, 3693–3703.

COMPARATIVE EXAMPLE 1

The procedure described in example 2 is repeated with the modification that 0.03 part of 1-ethynyl-1-cyclohexanol (which corresponds to 92 mol of alkynol per mole of platinum) was added instead of inhibitor 1.

COMPARATIVE EXAMPLE 2

The procedure described in example 2 is repeated with the modification that 0.024 part of 3-methyl-1-butyne-3,4-diol was added instead of inhibitor 1.

COMPARATIVE EXAMPLE 3

The procedure described in example 2 is repeated with the modification that 0.047 part of 3-methyl-1-dodecyn-3-ol was added instead of inhibitor 1.

EXAMPLE 4

Crosslinking and Pot Life Experiments

The thermal curing properties of the silicone materials prepared in examples 2 and 6 and in comparative examples 1, 2 and 3 were measured using a Dynamic Analyzer RDA II, from Rheometrics with a heating curve of from 30 to 200° C. and at a heating rate of 5° C./minute. The time and the temperature which corresponds to the 50% value of the maximum torque was defined as the $t_{50}$ value [min] or $T_{50}$ value [° C.]. For the quantitative determination of the pot life (PL), the formulations prepared were each stored at room temperature (RT) and 50° C., the time (measured in days) taken for doubling of the initial value of the viscosity being determined. The thin-film pot lives (TFL) are determined by applying the silicone material by means of 100 μm doctor blade to a glass plate and storing it at room temperature. The time taken until the respective material was no longer tacky was determined. The results of the measurements are shown in Table 1.

TABLE 1

| Mixture | $t_{50}$ [min] | $T_{50}$ [° C.] | PL at 50° C. | PL at RT | TFL |
|---|---|---|---|---|---|
| Example 2 | 19.0 | 120.5 | 2 d | 57 d | 12 d |
| Comp. example 1 | 18.8 | 119.4 | 0.5 d | 12 d | 0.2 d |
| Comp. example 2 | 20.1 | 125.9 | 1 d | 4 d | 1.5 d |
| Comp. example 3 | 19.9 | 125.1 | 1 d | 32 d | 1 d |
| Example 6 | — | 127.4 | 4 d | 73 d | 18 d |

As is evident from table 1, by far the longest pot lives are obtained with the materials according to examples 2 and 6, on storage at RT, on storage at 50° C., and in the thin film storage, while the $T_{50}$ and $t_{50}$ values of all samples are in a similar range.

In order to investigate the influence of the volatility of the different inhibitors on the pot lives and crosslinking characteristic during storage, the mixtures from example 2 and comparative example 1 were each prepared without the Karstedt catalyst and stored for 2 months in a PE beaker at room temperature. After storage, the Karstedt catalyst was added to the mixture and the curing properties and pot lives were determined on the basis of the procedures described above. The results are shown in table 2.

TABLE 2

| Mixture | $T_{50}$ [° C.] | PL at 50° C. | PL at RT | TFL |
|---|---|---|---|---|
| Example 2 after storage | 118.5 | 2 d | 53 d | 11 d |
| Comparative Example 1 after storage | 114.1 | 0.2 d | 5 d | 0 d |

As is evident from the table, the curing properties and pot lives remain relatively constant in the case of the materials according to example 2 whereas the pot lives are greatly reduced in the case of comparative example 1 owing to the volatility of the inhibitor.

EXAMPLE 3

589.4 parts of a vinyldimethylsilyloxy-terminated polydimethylsiloxane having a Brabender plasticity of 630 mkp, corresponding to an average molar mass of about 500,000 g/mol, were mixed with 252.6 parts of a hydrophobic pyrogenic silica having a BET surface area of 300 m$^2$/g and a carbon content of 3.95% by weight, which was metered in portions, for 4 hours in a kneader to give homogeneous material.

500 parts of the base material thus obtained were mixed on a roll at a temperature of 20° C. with 5.4 parts of inhibitor 1, 7.5 parts of SiH crosslinking agent and 0.002 part of Karstedt catalyst (1% strength, based on platinum and dissolved in toluene) to give a homogeneous material, the SiH crosslinking agent being a copolymer of dimethylsilyloxy, methylhydrogensilyloxy and trimethylsilyloxy units, having a viscosity of 310 mPa·s at 25° C. and a content of Si-bonded hydrogen of 0.46% by weight.

COMPARATIVE EXAMPLE 4

The procedure described in example 3 is repeated with the modification that 0.25 part of 1-ethynyl-1-cyclohexanol was added instead of inhibitor 1. Thus, the same molar amounts of alkynol groups are present in example 3 and comparative example 4.

The thermal curing properties of the silicone materials prepared in example 3 and comparative example 4 were measured using a Goettfert elastograph. or for the quantitative determination of storability, the formulations prepared were stored at room temperature (RT) and 50° C., the time (measured in days) taken until doubling of the initial value of the viscosity being determined. The results of the measurements are shown in table 3.

TABLE 3

| Mixture | $a_T$ [°C.] | $t_{90}$ [s] | PL at 50° C. | PL at RT |
|---|---|---|---|---|
| Example 3 | 119 | 30 | 5 d | 82 d |
| Comp. Example 4 | 118 | 31 | 1.5 d | 8 d |

The initiation temperature $a_T$ was determined at a heating rate of 10° C./min. The temperature which corresponds to the 4% value of the maximum torque was defined as the initiation temperature. The determination of the $t_{90}$ value was effected according to DIN 53529 T3. The duration from the beginning of curing to 90% ($t_{90}$ value) of the maximum torque was determined at 180° C. As is evident from table 3, the materials according to example 3 have substantially longer pot lives with similar crosslinking characteristics.

EXAMPLE 5

25.6 parts of H—C≡C—C(OH)(CH$_3$)—(CH$_2$)$_3$—OH, 33.2 parts of 3-chloropropyltrimethylsilane, 3.0 parts of sodium iodide, 27.6 parts of anhydrous potassium carbonate and 200 parts of dried methylethylketone were mixed and refluxed under a nitrogen atmosphere for 48 hours. Thereafter, the mixture was cooled to room temperature and filtered and the filtrate was evaporated under a vacuum from an oil pump at room temperature. The residue was subjected to fractional distillation in vacuo. According to NMR and MS, the compound obtained has the following structure:
H—C≡C—C(OH)(CH$_3$)—(CH$_2$)$_3$—O—(CH$_2$)$_3$Si(CH$_3$)$_3$.

EXAMPLE 6

In a laboratory kneader, 255 parts of a vinyldimethylsilyloxy-terminated polydimethylsiloxane having a viscosity of 20,000 mm$^2$/s was initially heated to 150° C., and 180 parts of a hydrophobic pyrogenic silica having a BET surface area of 300 m$^2$/g and a carbon content of 3.95% by weight were added. A highly viscous material formed, which was subsequently diluted with 165 parts of the polydimethylsiloxane mentioned above. Volatile components were removed by kneading in vacuo (10 mbar) at 150° C. for one hour.

488.1 parts of the base material thus prepared were mixed on a roll with 0.280 part of inhibitor from example 5 (which corresponds to 92 mol of alkynol per mole of platinum), 10.95 parts of SiH crosslinking agent and 0.244 part of Karstedt catalyst (based on platinum: 1% strength in toluene) to give a homogeneous material, the SiH crosslinking agent being a copolymer of phenylmethylsilyloxy and methylhydrogensilyloxy and trimethylsilyloxy units, having a viscosity of 400 mm$^2$/s and a content of Si-bonded hydrogen of 0.46% by weight.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. An organosilicon compound having alkynol groups and comprising units of the formula

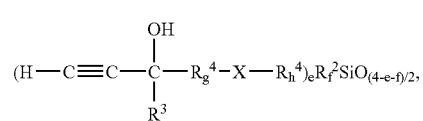

$$(H-C\equiv C-\underset{R^3}{\underset{|}{\overset{OH}{\overset{|}{C}}}}-R_g^4-X-R_h^4)_e R_f^2 SiO_{(4-e-f)/2}, \quad (III)$$

in which

R$^2$ are identical or different and are a hydrogen atom, a radical —OR$^5$, or an optionally substituted hydrocarbon radical, R$^3$ are identical or different and are a hydrogen atom, a halogen atom, a radical —OR$^5$, or a monovalent, optionally substituted hydrocarbon radical, R$^4$ are identical or different and are a divalent organic radical, X are identical or different and are —O—, —S—, —OC(=O)—, —N(R$^6$)— or —N(R$^6$)—C(=O)—, R$^5$ are identical or different and are a hydrogen atom or a monovalent, optionally substituted hydrocarbon radical, R$^6$ are identical or different and are a hydrogen atom or a monovalent, optionally substituted hydrocarbon radical, e is 0, 1, 2 or 3, f is 0, 1, 2 or 3, g is 0 or a positive integer and h is 0 or a positive integer, with the proviso that the sum e+f is less than or equal to 3 and the organosilicon compound has at least one unit of the formula (III) where e is not zero.

2. The organosilicon compound of claim 1, wherein X is —O—.

3. The organosilicon compound of claim 1, wherein the sum e+f<3.

4. The organosilicon compound of claim 2, wherein the sum e+f<3.

5. A crosslinkable material comprising
(A) one or more compounds which contain radicals having aliphatic carbon-carbon multiple bonds,
(B) at least one organosilicon compound having Si-bonded hydrogen atoms,
(C) at least one organosilicon compound of claim 1 having alkynol groups and containing units of the formula (III),

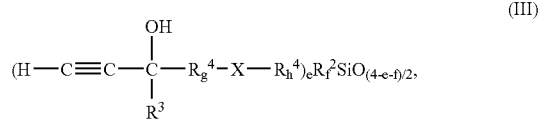

in which
$R_2$ are identical or different and are a hydrogen atom, a radical —$OR^5$, or an optionally substituted hydrocarbon radical,
$R^3$ are identical or different and are a hydrogen atom, a halogen atom, a radical —$OR^5$, or a monovalent, optionally substituted hydrocarbon radical,
$R^4$ are identical or different and are a divalent organic radical,
X are identical or different and are —O—, —S—, —OC(=O)—, —N($R^6$)— or —N($R^6$)—C(=O)—,
$R^5$ are identical or different and are a hydrogen atom or a monovalent, optionally substituted hydrocarbon radical,
$R^6$ are identical or different and are a hydrogen atom or a monovalent, optionally substituted hydrocarbon radical,
e is 0, 1, 2 or 3,
f is 0, 1, 2 or 3,
g is 0 or a positive integer and
h is 0 or a positive integer,
with the proviso that the sum e+f is less than or equal to 4 and the organosilicon compound has at least one unit of the formula (III) where e is not zero, and
(D) at least one catalyst which promotes the addition of Si-bonded hydrogen at an aliphatic multiple bond.

6. The crosslinkable material of claim 5, wherein at least one component (A) comprises an aliphatically unsaturated organosilicon compound.

7. The crosslinkable material of claim 5, wherein component (C) is present in an amount of from 0.0001 to 70% by weight, based on the weight of component (A).

8. The crosslinkable material of claim 5, comprising:
(A) at least one compound which contain radicals having aliphatic carbon-carbon multiple bonds,
(B) at least one organopolysiloxane having Si-bonded hydrogen atoms,
(C) at least one organopolysiloxane having alkynol groups and containing units of the formula (III) where the sum of e+f≦3,
(D) at least one catalyst which promotes the addition of Si-bonded hydrogen and an aliphatic multiple bond, and optionally,
(E) reinforcing fillers.

9. The crosslinkable material of claim 5, comprising:
(A) substantially linear compound(s) which have on average at least two radicals having aliphatic carbon-carbon multiple bonds,
(B) organopolysiloxanes having on average at least two Si-bonded hydrogen atoms,
(C) organopolysiloxanes having alkynol groups and containing units of the formula (III),
(D) at least one catalyst which promotes the addition of Si-bonded hydrogen at an aliphatic multiple bond,
(E) optionally reinforcing fillers,
(F) optionally further components, and
(G) optionally inhibitors and/or stabilizers.

10. The crosslinkable material of claim 5, wherein the sum of e+f is less than or equal to 3.

11. A process for producing a molding, comprising adding to a mold a crosslinkable material comprising:
(A) one or more compounds which contain radicals having aliphatic carbon-carbon multiple bonds,
(B) at least one organosilicon compound having Si-bonded hydrogen atoms,
(C) at least one organosilicon compound of claim 1 having alkynol groups and containing units of the formula (III),

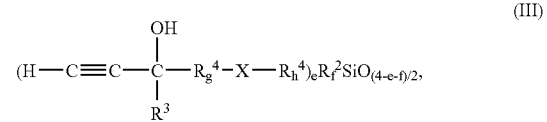

in which
$R_2$ are identical or different and are a hydrogen atom, a radical —$OR^5$, or an optionally substituted hydrocarbon radical,
$R^3$ are identical or different and are a hydrogen atom, a halogen atom, a radical —$OR^5$, or a monovalent, optionally substituted hydrocarbon radical,
$R^4$ are identical or different and are a divalent organic radical,
X are identical or different and are —O—, —S—, —OC(=O)—, —N($R^6$)— or —N($R^6$)—C(=O)—,
$R^5$ are identical or different and are a hydrogen atom or a monovalent, optionally substituted hydrocarbon radical,
$R^6$ are identical or different and are a hydrogen atom or a monovalent, optionally substituted hydrocarbon radical,
e is 0, 1, 2 or 3,
f is 0, 1, 2 or 3,
g is 0 or a positive integer and
h is 0 or a positive integer,
with the proviso that the sum e+f is less than or equal to 4 and the organosilicon compound has at least one unit of the formula (III) where e is not zero, and
(D) at least one catalyst which promotes the addition of Si-bonded hydrogen at an aliphatic multiple bond,
and crosslinking said crosslinkable composition.

12. The process of claim 11, wherein at least one component (A) comprises an aliphatically unsaturated organosilicon compound.

13. The process of claim 11, wherein component (C) is present in an amount of from 0.0001 to 70% by weight, based on the weight of component (A).

14. The process of claim 11, comprising:
(A) at least one compound which contain radicals having aliphatic carbon-carbon multiple bonds,
(B) at least one organopolysiloxane having Si-bonded hydrogen atoms,
(C) at least one organopolysiloxane having alkynol groups and containing units of the formula (III) where the sum of $e+f \leqq 3$,
(D) at least one catalyst which promotes the addition of Si-bonded hydrogen and an aliphatic multiple bond, and optionally,
(E) reinforcing fillers.

15. The process of claim 11, comprising:
(A) substantially linear compound(s) which have on average at least two radicals having aliphatic carbon-carbon multiple bonds,
(B) organopolysiloxanes having on average at least two Si-bonded hydrogen atoms,
(C) organopolysiloxanes having alkynol groups and containing units of the formula (III),
(D) at least one catalyst which promotes the addition of Si-bonded hydrogen at an aliphatic multiple bond,
(E) optionally reinforcing fillers,
(F) optionally further components, and
(G) optionally inhibitors and/or stabilizers.

16. The process of claim 11, wherein component (C) is present in an amount of 0.02 weight percent to about 10 weight percent, based on the weight of component (A).

* * * * *